United States Patent [19]

Lindley

[11] Patent Number: 4,739,749

[45] Date of Patent: Apr. 26, 1988

[54] ORTHOSPINAL CHAIR

[76] Inventor: William L. Lindley, P.O. Box 300109, Houston, Tex. 77230

[21] Appl. No.: 846,207

[22] Filed: Mar. 21, 1986

[51] Int. Cl.[4] .................... A61F 5/00

[52] U.S. Cl. .................... 128/71; 128/75

[58] Field of Search .................... 128/69, 70, 71, 24 R, 128/75; 272/72

[56] References Cited

U.S. PATENT DOCUMENTS

| | | | |
|---|---|---|---|
| 1,622,313 | 3/1927 | Gellhorn | 128/71 X |
| 3,081,085 | 3/1963 | De Girolamo | 128/24 R |
| 3,286,708 | 11/1966 | Gartner | 128/71 X |
| 3,570,479 | 3/1971 | Horn | 128/71 |
| 3,590,812 | 7/1971 | Larson | 128/71 X |
| 3,986,499 | 10/1976 | Fischer | 128/71 |
| 4,103,681 | 8/1978 | Shanley | 128/71 |
| 4,214,790 | 7/1980 | Sieber | 128/70 X |
| 4,563,000 | 1/1986 | Gall | 272/72 |

FOREIGN PATENT DOCUMENTS

| | | | |
|---|---|---|---|
| 1121687 | 8/1956 | France | 128/71 |

*Primary Examiner*—Edgar S. Burr
*Assistant Examiner*—Moshe I. Cohen
*Attorney, Agent, or Firm*—Pravel, Gambrell, Hewitt, Kimball & Krieger

[57] ABSTRACT

An orthospinal chair for exercising the spinal column and back muscles by placing tension on the spine through partial inversion. The orthospinal chair allows partial inversion of a person in a supine, bent-knee position at an easily controllable angle. The user of the orthospinal chair is retained in a supine, bent-knee position by a restraining strap secured across the hip area which allows the person to apply tension while in a partially inverted position to relieve back pain and strengthen back muscles.

5 Claims, 1 Drawing Sheet

ORTHOSPINAL CHAIR

FIELD OF THE INVENTION

This invention relates to orthopedic exercise devices, and more specifically an orthospinal chair to exercise the spinal column in a tension or elongated position.

BACKGROUND OF THE INVENTION

Experts estimate that eighty percent of the United States population is afflicted with low back pain at some time in their lives. It has been reported that Americans spend approximately five billion dollars annually for treatment of back pain, often on treatment which is ineffective. In recent years the desirability of exercise of the back muscles and the spinal column in a tension or elongated position as opposed to compression has been proposed. The exercising of the back muscles and spinal column under tension has been found to allow for the proper alignment or realignment of the spinal column by removing the compressive load from pinched nerves and to strengthen and straighten contracted muscles in the lower back region.

Typical treatment for lower back pain includes not only occupational and physiological therapy but also physical therapy. The previously known physical therapy equipment used to provide tension on the spinal column and back muscles typically is expensive and complicated. Such equipment requires a skilled technician to adjust and operate. Thus, treatment for lower back pain has been an expensive endeavor.

In recent years the advantages of removing compression in alleviating or avoiding lower back pain have become more commonly known to the general public. This has resulted in the development of apparatus for personal home use which removes the normal compressive forces from the spinal column. Such apparatus typically include special "boots" or fittings for the ankles which are designed to allow a person to hang upside down by the feet. While this position does remove the compressive forces from the spinal column, the effects on blood flow from hanging completely upside down may be dangerous and it is believed that most people find the hanging upside down position extremely uncomfortable Furthermore, the apparatus to allow such a position is typically complex and requires a user to have above average agility and strength to safely use the equipment without supervision.

The difficulty of using such home inversion equipment and the uncomfortable position of hanging by the feet has limited public acceptance of such equipment and treatment, especially by the elderly or injured who could most often benefit from the treatment.

The present invention provides a simplified apparatus for applying tension to the spinal column and back muscles which allows for easy adjustment and safe, unsupervised use. The extent of inversion is easily controlled and the user is held in a bent knee, partially inverted position with a seatbelt-like restraint strap. The present invention can be easily and safely used without supervision because the user is not suspended in a totally inverted position but is partially inverted in a more comfortable supine, bent knee position. The apparatus allows for simple movement of the person's arms and legs to initiate the inversion and to return the person to a normal upright sitting position.

SUMMARY OF THE INVENTION

The present invention is related to a new and improved apparatus for exercising the spinal column and back muscles by placing tension on the spine to allow elongation of the spinal column and back muscles The present invention allows partial inversion of a person in a supine, bent knee position at an easily controllable angle to allow for safe and comfortable inversion therapy for back ailments.

The apparatus of the present invention includes a support to be located on the floor which has a stop, preferably adjustable, to control the extent of inversion and preferably a kick bar to facilitate inversion. A chair board is pivotally mounted on the support and a retention belt is provided therewith. A person undergoes therapy by lying on the chair board with the restraint strap secured, and pivoting the board to a partially inverted position while his or her body is in a supine, bent knee position The person can then apply tension to his body by pulling against the retention belt to relieve back pain and strengthen back muscles.

DESCRIPTION OF THE PREFERRED EMBODIMENT

Figure 1:
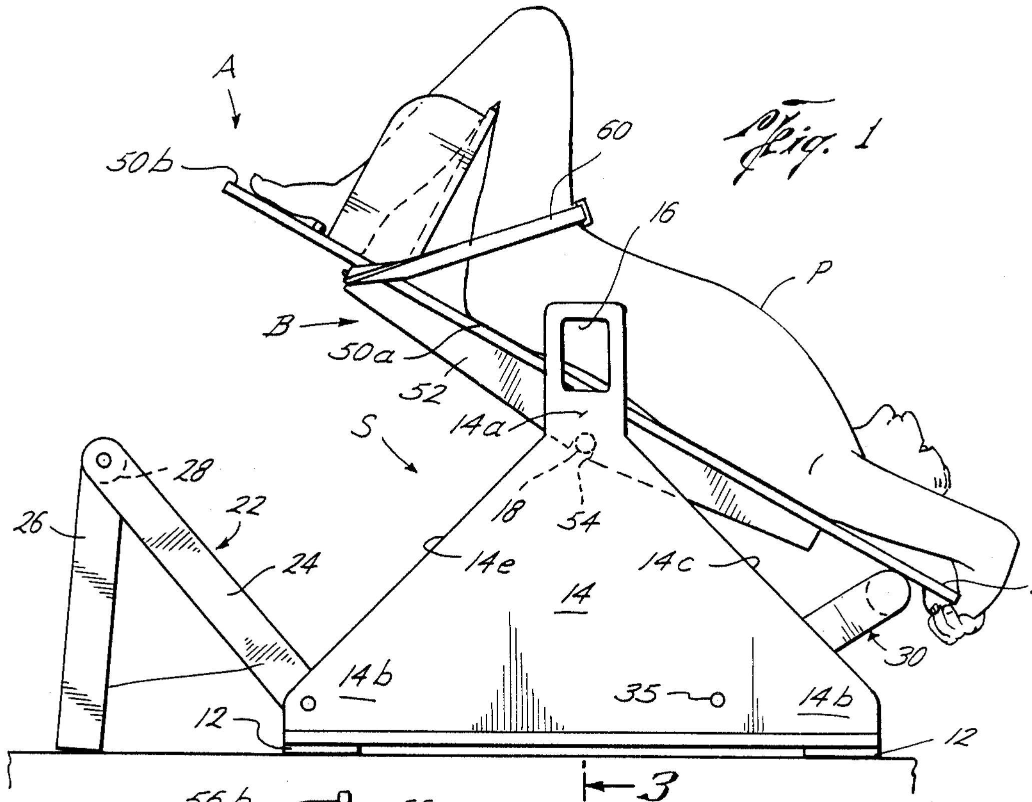
FIG. 1 is a side plan view of the present invention.

The apparatus A of the present invention allows a person P to easily orient oneself in a supine, bent knee, partially inverted position as shown in FIG. 1. The apparatus A includes two main sections, a support S and a chair board B.

Support S provides a stable base for the apparatus. Support S is preferably made up of a rectangular shaped base 10 which can include feet 12 which rest on the floor. Extending upwardly from two opposite sides of base 10 are triangularly shaped sides 14. Each side 14 terminates at its upper apex **14*a* in a handhold 16, which is more fully described below. Extending between sides 14 at the upper apex 14*a* adjacent handhold 16 is pivot rod 18. Spacer member 19 is secured inside of each side 14 and each terminates below the handhold 16 to provide a space between each handhold 16 and the board B to prevent a person from having his or her fingers pinched between the board B and the sides 14 when gripping the handholds 16. A vertical laterally extending brace 20 is secured to and between the spacer members 19** to rigidify the structure so that the weight of a person P can be supported with safety.

Extending from a lower apex **14*b* of sides 14 is a kick bar 22 which includes a pair of lateral extensions 24 each pivotally mounted at one end 24*a* to a side 14 and pivotally mounted at the other end 24*b* to a vertical brace 26 and joined by a cross member 28. One lateral extension 24 and one vertical brace 26 are attached to each side 14 and joined by cross member 28. The kick bar 22 allows a person P to push against the kick bar 22** with the feet to begin the pivotal movement of chair board B described below.

A pivotal stop 30 is pivotally connected to sides 14 approximately midway between braces 20 and apex **14*c***.

Pivotal stop 30 includes a pair of side bars 32 each pivotally attached at one end 32a to a side 14 and joined at the other end 32b by a cylindrical bar 34. A pivot limiting block 36 is mounted on each side 14 adjacent the pivotal connection 35 of pivot stop 30 to limit movement of pivot stop 30 from its stored position (FIG. 2) to its stop position (FIG. 1).

The triangular shape of sides 14 is preferably such that upwardly extending edges 14c form an angle of approximately forty-five degrees with the base 10. This corresponds to the maximum angle of pivot of chair board B as described below.

Chair board B includes a rectangular back 50 of a length sufficient to support a person in a supine bent knee position as shown in FIG. 1. Back 50 is reinforced with truss elements 52 mounted along each long side 50a of back 50. Each truss element 52 includes a notch 54 located approximately at the longitudinal midpoint of the back 50. The notches 54 are adapted to fit over pivot rod 18. Extending from back 50 approximately one-quarter of the distance along back 50 from end 50b is seat 56. Seat 56 typically includes a platform 56a perpendicular to back 50 and two braces 56b positioned near the side edges of the board 50. Mounted to back 50 between seat 56 and the end of back 50b is a heel bar 58. Heel bar 58 provides a stop for the heels of the person using the apparatus to assist the user in maintaining the bent knee position shown in FIG. 1 when the person stretches to place the body in tension.

A restraining strap 60 is mounted to chair board B adjacent the attachment point of seat 56. The restraining strap 60 assists the user in maintaining the bent knee position when stretching, and, more importantly, it confines and supports the body of the user at the hip region so that the user's lower back is forced against the board while the user uses his or her arms at the end of the board to develop tension on the spine and back muscles.

Chair board B is preferably wider at the head end (right hand end as seen in the drawings) to enable it to contact the edges 14c of support S so that chair board B will not pivot to an angle greater than the approximately forty-five degree angle of edge 14c from the floor when the stop 30 is in the storage or retracted position.

The orientation of the notches 54 in truss elements 52 is at approximately the longitudinal midpoint of chair board B. Thus, back 50, absent seat 56, would balance when oriented over pivot bar 18. The location of seat 56 results in an imbalance tending to pivot end 50b of chair board B downwardly (counterclockwise) until the end 50b contacts the floors or the support S which is the unloaded position.

Figure 2:
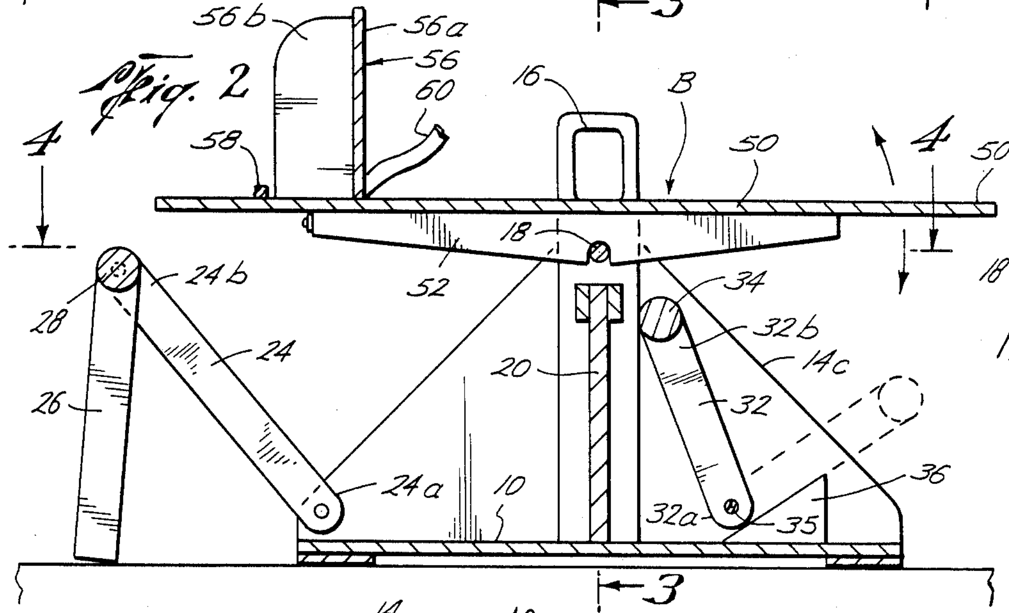
FIG. 2 is a side view, partly in cross-section, of the present invention.
Figure 3:
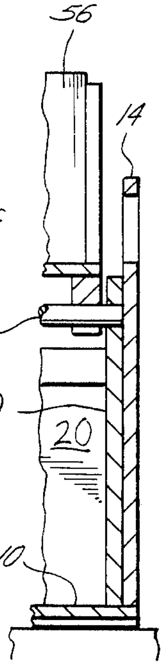
FIG. 3 is a partial cross-sectional view along line 3—3 of FIG. 2.
Figure 4:
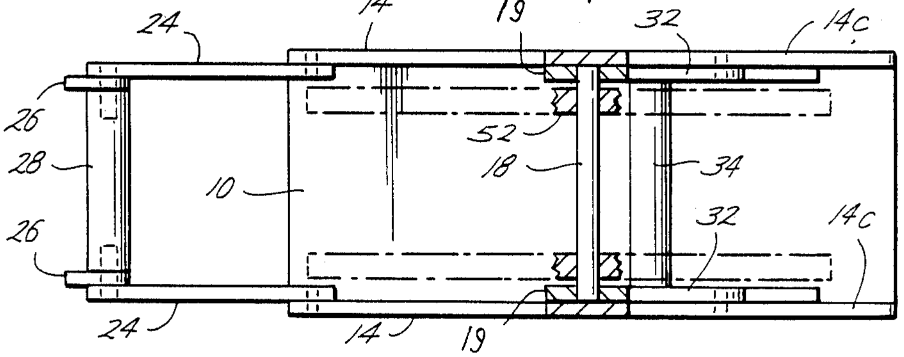
FIG. 4 is a cross-sectional view along line 4—4 of FIG. 2.

In the use of the apparatus, the user first positions pivot stop 30 to that shown in FIG. 1 to limit the extent of inversion, if that is desired. When pivot stop 30 is oriented as shown in FIG. 1, the angle of inversion is limited by contact of chair board B with pivot stop 30. With pivot stop 30 in the stored position as is shown in FIG. 2, chair board B is able to pivot to an inverted position at an angle of approximately forty-five degrees with the floor, as previously explained. Therefore, the greater angle of inversion can be selected by putting the stop 30 in the retracted position. It will be understood that the particular angles thus provided may be different, so long as the person can reach one or more partially inverted positions.

The person P then sits upon chair 56, and buckles restraining strap 60 about his or her hips. To pivot into the partially inverted position as shown in FIG. 1, the person pushes upon kick bar 28 with his or her feet and raises his or her arms over the head. Raising the arms over the head transfers the center of gravity of the person P from the chair side 50b of chair board B to the opposite side, causing pivoting of chair board B about pivot bar 18 to the FIG. 1 position. Person P, by placing his or her feet on heel bar 58, assumes the desired bent knee position shown in FIG. 1 which prevents sliding along chair back 50 under restraining strap 60. Person P is thus held in the partially inverted position by a seat-belt-like restraining strap 60 which supports the lower pelvic/upper thigh region in a comfortable, safe manner.

The person P has complete control of the pivotal movement through movement of the arms and legs. Handholds 16 are provided to assist in shifting the person's center of gravity to pivot into or out of the partially inverted position shown in FIG. 1. Such pivotal action is further assisted by the natural motion of straightening the legs. Release from the partially inverted position requires simple arm and leg movement to shift the center of gravity of the person P. The user may grip the handholds 16 and initiate the pivotal movement from the tension position of FIG. 1 to the unloaded position where the user is in a substantially upright position (not shown).

In use, the user pulls his or her body towards end 50c while in the inversion position of FIG. 1. Because the strap 60 restrains the hips from moving, the lower back is pulled down against the board, causing a straightening of the spine and placing it under tension. Repeated stretching and relaxing exercises the back muscles to strengthen them, so that the relief from the back pain is not only while on the board, but can continue after using the apparatus by reason of the stretched spine and the stronger back muscles.

The apparatus of the present invention may have a drive motor (not shown) operably connected to the board B, preferably at the pivot bar 18 location to effect the pivoting action of the back board. The motorized version allows for a greater range of control of the angle of inversion and allows a slower, more precise control of the pivotal action. The motorized version is desirable for person who may have physical impediments or lack the strength or coordination to manually control the pivoting of the board B.

The apparatus A of the present invention thus provides for partial inversion to relieve compression on the spinal column in a safe and easily controlled environment.

It should be understood that the foregoing description and the drawings of the invention are not intended to be limiting, but are only exemplary of the inventive features which are defined in the claims.

What is claimed is:

1. An apparatus adapted to allow elongation and stretching of the spinal column and strengthening of the back muscles, which comprises:

support means adapted to be positioned on a base;

a substantially flat board positioned on said support means and having an upper surface;

knee positioning means extending upwardly from said surface of said board to position the legs of a user in a substantially fully bent knee position on the board with the knees raised above said surface of said board and with the feet substantially at said surface of said board;

heel restraint means on said board for engagement by the heels of the user when the legs of the user are in said substantially fully bent knee position;

hip restraint means mounted to said board for confining the body of the user at the hips and for restraining movement of the hips relative to said board;

said hip restraint means being located in proximity to said knee positioning means to hold the hip region of the user's lower back against the board and to restrain movement relative to the board with the knees in the bent knee position and with the heels of the user restrained against movement away from the user's hip region, whereby when the user stretches on the board the back is supported on the board, the hips are restrained, and the heels are supported to enable the user to apply a stretching thrust and twist to the spine to relieve tension and strengthen the back muscles; and pivot means on said support means for pivotally moving said board from a first substantially upright position to a second position supporting the user in a partially inverted position restrained by said restraint means.

2. The apparatus of claim 1, further including stop means pivotally mounted to said support means to limit the inclination of said board in said second position.

3. The apparatus of claim 1, wherein said knee-positioning means is a chair on said board to receive a user in said first substantially upright position, and to also permit a user to disembark in that position.

4. The apparatus of claim 1, wherein said restraint means comprises an adjustable belt mounted to said board adjacent said knee positioning means adapted to encircle a person lying on said board to maintain the hips of said person adjacent said knee positioning means when said board is pivoted to said second partially inverted position.

5. The apparatus of claim 1, including a heel bar disposed on said board adjacent said knee positioning means but on the opposite side thereof from said hip restraint means whereby when said board is pivoted to said second partially inverted position, orientation of the user's feet on said heel bar assists the user in maintaining the user's legs in a bent-knee position over the knee positioning means.

* * * * *